United States Patent
Vaiarello et al.

(10) Patent No.: US 12,302,070 B2
(45) Date of Patent: May 13, 2025

(54) IMPLANTABLE HEARING DEVICE FOR ENHANCING THE HEARING CAPABILITY OF A USER

(71) Applicant: Oticon Medical A/S, Smørum (DK)

(72) Inventors: Yannick Vaiarello, Vallauris (FR); Franck Mattioli, Vallauris (FR); Julien Venet, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 267 days.

(21) Appl. No.: 17/965,543

(22) Filed: Oct. 13, 2022

(65) Prior Publication Data
US 2023/0119384 A1    Apr. 20, 2023

(30) Foreign Application Priority Data
Oct. 14, 2021 (EP) .................... 21202690

(51) Int. Cl.
*H04R 25/00*    (2006.01)
(52) U.S. Cl.
CPC ......... *H04R 25/609* (2019.05); *H04R 25/606* (2013.01); *H04R 2225/51* (2013.01); *H04R 2225/57* (2019.05)
(58) Field of Classification Search
CPC .............. H04R 25/609; H04R 25/606; H04R 2225/51; H04R 2225/57; H04R 2225/49; H04R 2225/67; A61N 1/37223; A61N 1/3787
See application file for complete search history.

(56) References Cited

U.S. PATENT DOCUMENTS

| | | | |
|---|---|---|---|
| 7,775,964 B2 * | 8/2010 | Miller, III | H04R 25/606 600/25 |
| 2009/0171420 A1 | 7/2009 | Brown et al. | |
| 2009/0247814 A1 * | 10/2009 | Parker | H04R 25/70 600/25 |
| 2011/0257703 A1 | 10/2011 | Kerber et al. | |
| 2014/0241557 A1 * | 8/2014 | Martius | H01Q 21/24 381/323 |
| 2019/0348863 A1 | 11/2019 | De Masi et al. | |
| 2020/0069944 A1 | 3/2020 | Gnansia et al. | |

OTHER PUBLICATIONS

Extended European Search Report issued in Application No. 21202690.0 dated May 4, 2022.

* cited by examiner

*Primary Examiner* — Tuan D Nguyen
(74) *Attorney, Agent, or Firm* — Birch, Stewart, Kolasch & Birch, LLP

(57) ABSTRACT

An implantable hearing device for enhancing the hearing capability of a user is disclosed. The implantable hearing device may include: at least one housing having a top side to be substantially directed towards the skin of a user and at least one bottom side to be substantially directed opposite to the top side, at least one implant antenna element for inductively connecting the implantable hearing device to an external device via a magnetic field, in particular to at least one external hearing device. The bottom side of the at least one housing at least partly is of metallic material, and the top side of the at least one housing at least partly is of nonmetallic material. Additionally, an implantable hearing system is disclosed.

18 Claims, 3 Drawing Sheets

IMPLANTABLE HEARING DEVICE FOR ENHANCING THE HEARING CAPABILITY OF A USER

FIELD

The present disclosure relates to an implantable hearing device for enhancing the hearing capability of a user. More particularly, the disclosure relates to an implantable hearing device for enhancing the hearing capability of a user comprising: at least one housing comprising a top side to be substantially directed towards the skin of a user and at least one bottom side to be substantially directed opposite to the top side, at least one implant antenna element for inductively connecting the implantable hearing device to an external device via a magnetic field, in particular to at least on external hearing device, wherein the bottom side of the at least one housing at least partly is of metallic material, and wherein the top side of the at least one housing at least partly is of nonmetallic material.

BACKGROUND

Any discussion of the prior art throughout the specification should in no way be considered as an admission that such prior art is widely known or forms parts of common general knowledge in the respective field.

The type of implantable hearing devices and the range of functions performed thereby have increased over the years. Therefore, many components of such implantable hearing devices receive power and/or data over a wireless transcutaneous link from external devices that are operated in conjunction with the implantable hearing device.

Implantable hearing devices for enhancing the hearing capability of a user may for example be connected with at least one external device in order to supply the implanted hearing device with energy. The energy may for example be transmitted via a magnetic field between at least one implant antenna element and at least one external device, in particular via at least one inductive link between the at least one implant antenna element and the at least one external device.

Since the implantable hearing devices regularly have to be at least partly biocompatible, the at least one housing of the implantable hearing device at least partly comprises a metallic material. However, by providing a metallic housing, the at least one implant antenna element may be at least partly hindered to reliably establish a connection to an external device via a magnetic field.

It is known from the state of the art to source the at least one implant antenna element out of the at least one housing in order to improve the connection between the at least one implant antenna element to an external device. Such a solution in particular is adverse with regard to the size of the implantable hearing device since an arrangement of the at least one implant antenna element outside of the at least one housing increases the total size of the implantable hearing device.

Alternatively, it is known from the state of the art to provide an implantable hearing device comprising a housing with a top side, wherein the material of the top side at least partly is of nonmetallic material. This configuration also may cause a reduced performance of the connection between the at least one implant antenna element and the external device since the performance of the magnetic field may be reduced due to the metallic material of the bottom part of the housing. This may negatively affect the efficiency between the at least one implant antenna element and the external device. Such an efficiency may be increased by increasing the distance between the at least one implant antenna element and the bottom part of the housing, whereas an increase in such distance may cause an undesirable increasing in thickness of the implantable hearing device.

Therefore, there is a need to provide an implantable hearing device that provides a compact design and also enables a reliable connection between the at least one implant antenna element and at least one external device.

SUMMARY

According to an aspect, the implantable hearing device for enhancing the hearing capability of a user may comprise at least one housing comprising a top side to be substantially directed towards the skin of a user and at least one bottom side to be substantially directed opposite to the top side, at least one implant antenna element for inductively connecting the implantable hearing device to an external device via a magnetic field, in particular to at least on external hearing device, wherein the bottom side of the at least one housing at least partly is of metallic material, and wherein the top side of the at least one housing at least partly is of nonmetallic material. The implantable hearing device may further comprise at least one magnetic sheet arranged substantially between the at least one implant antenna element and the bottom side of the at least one housing, wherein the at least one magnetic sheet is configured to affect the magnetic field of the at least one implant antenna element.

The top side of the at least one housing may in particular be directed into the direction of the at least one external device, in particular into the direction of the at least one external hearing device. Preferably, substantially the whole top side of the at least one housing is of nonmetallic material. By at least partly providing the nonmetallic top side of the at least one housing, the connection between the at least one implant antenna element and the at least one external device may be improved. In particular, since the nonmetallic material of the top side of the at least one housing may enable the at least one implant antenna element to be reliably connected to and external device via a magnetic field.

The bottom side of the at least one housing may substantially be of metallic material which in particular may be beneficial with regard to the biocompatibility of the implant hearing device. Preferably, not only the bottom side of the at least one housing, but also the sides of the at least one housing may be of metallic material.

Preferably, at least one magnetic sheet is arranged substantially between the at least one implant antenna element and the bottom side of the at least one housing, wherein the at least one magnetic sheet is configured to affect the magnetic field of the at least one implant antenna element. This allows for a compact design of the implantable hearing device while also enabling a reliable connection between the at least one implant antenna element and the external device, in particular the at least one external hearing device. By inserting at least one magnetic sheet between the at least one implant antenna element and the bottom side of the implantable hearing device, the magnetic field of the at least one antenna element may be altered. Hereby, the impact of the bottom side of the at least one housing comprising metallic material on the magnetic field may be at least partly reduced. In particular, if the bottom side of the at least one housing at least partly comprises a magnetic material with a high permeability, the magnetic field of the at least one antenna element may be otherwise negatively impacted. Preferably, the at least one magnetic sheet influences the magnetic field such that it is forwarded to the top side of the at least one housing and thus towards at least one external device which is for example arranged on the skin of a user. This may enable the implantable hearing device to use substantially the whole magnetic field correctly and therefore reduce the losses of the implantable hearing device or the implantable hearing system.

According to another aspect, an implantable hearing system may comprise at least one implantable hearing device and at least one external hearing device for being inductively connected to the at least one implant antenna element.

Preferably, the at least one implant antenna element may be inductively connected to the external device via a wireless transcutaneous link comprising a magnetic field. Said wireless transcutaneous link may be realized as an inductive link, with the external unit comprising at least one external antenna element with at least one primary coil and the at least one implantable antenna element comprising at least one secondary coil. The secondary coil preferably may be arranged in the housing of the implantable hearing device and the primary coil may be attached to the skin of the user such that the two coils are substantially in parallel planes on both sides (external and implantable positions) of the skin. Such systems may be referred to as TET links (TET-Transcutaneous Energy Transfer).

The implantable hearing device may comprise at least one housing, wherein the bottom side of the at least one housing at least partly is of titanium, in particular that the bottom side of the at least one housing is substantially composed of titanium. This allows for providing a bottom side of the at least one housing with sufficient strength characteristics and a relatively low modulus of elasticity. Additionally, titanium is biocompatible, in particular due to a low susceptibility to corrosion. It is also preferred that the bottom side of the at least one housing is at least partly of a titanium alloy, in particular that the bottom side of the at least one housing is substantially composed of a titanium alloy.

The implantable hearing device may comprise at least one housing, wherein the top side of the at least one housing at least partly is of ceramic material, in particular that the top side of the at least one housing is substantially composed of a ceramic material. This allows for providing a top side of the at least one housing which at least substantially does not adversely influence the connection of the at least one implant antenna element to the at least one external device, in particular to at least one external antenna element of the external device. Additionally, the ceramic material may provide a beneficial wear resistance and biochemical inertness.

The implantable hearing device may comprise at least one magnetic sheet, wherein the at least one magnetic sheet at least partly is of a ferrite material, in particular that the at least one magnetic sheet is substantially composed of a ferrite material. Hereby, a magnetic sheet may be provided which enables an influencing of the magnetic field of the at least one antenna element such that it is forwarded to the top side of the at least one housing and thus towards the at least one implant antenna element and/or towards the at least one external device which is for example arranged on the skin of a user. This may enable the implantable hearing device to use substantially the whole magnetic field correctly and therefore reduce the losses of the implantable hearing device or the implantable hearing system.

By providing at least one magnetic sheet which is at least partly of a ferrite material, the magnetic field propagation of the at least one implant antenna element may be improved. Additionally, also the magnetic field propagation of at least one external antenna element may be improved. Therefore, the overall efficiency of the connection between the implantable hearing device and the external device may be improved.

The at least one magnetic sheet of at least partly ferrite material may also lead to an improved radiation efficiency and also an improved inductance of the at least one implant antenna element and also reduce the interference of the at least one antenna element with the user of the implantable hearing device. Further, by providing a magnetic sheet of at least partly a ferrite material, the influence of mechanical and/or constructive changes to the implantable hearing device may be reduced.

The at least one implant antenna element may comprise at least one coil element and the form of the at least one magnetic sheet may substantially correspond to the form of the at least one coil element. The at least one coil element for example may comprise litz wires, wherein the at least one coil element may be arranged to transmit and/or receive energy. In particular, the at least one coil element may be a secondary coil. Due to the corresponding form of the at least one magnetic sheet to the at least one coil element, an effective redirecting of the magnetic field of the at least one coil element may be provided by the at least one magnetic sheet. In particular, the magnetic field of the at least one coil element may be directed towards the top side of the at least one housing and therefore towards the at least one external device. The form of the at least one coil element and the at least one magnetic sheet may be chosen depending on the space inside the housing and the coil performance envisaged.

The at least one coil element may be formed substantially circular and the at least one magnetic sheet may be formed substantially circular. A substantially circular design of the at least one magnetic sheet and the at least one coil element may be beneficial regarding the available space inside the at least one housing. In particular, the at least one housing also is of substantially circular shape.

The implantable hearing device may further comprise at least one printed circuit board. Electronic components, such as for example the at least one implant antenna element may be mounted on the at least one circuit board in a beneficial manner. The printed circuit board may be of a rigid or an at least partly flexible material. The printed circuit board may comprise at least one electronic circuit. The grounding plane for the at least one antenna element may be arranged on the at least one printed circuit board, in particular on the at least one electronic circuit of the at least one printed circuit board or between the at least one electronic circuit and the at least one magnetic sheet.

The at least one printed circuit board may be arranged substantially between the at least one magnetic sheet and the bottom side of the at least one housing. This allows for the at least one magnetic sheet to substantially shield the printed circuit board and components arranged on the printed circuit board from the magnetic field of the at least one implant antenna element.

The printed circuit board may at least partly embed the at least one implant antenna element and/or the at least one magnetic sheet. This allows for a compact design of the implantable hearing device. Preferably, the at least one antenna element may be embedded into a top side of the at least one printed circuit board, wherein the top side of the at least one printed circuit board substantially may be directed towards the top side of the at least one housing. Preferably, at least one electronic circuit may be at least partly embedded into a bottom side of the at least one printed circuit board, wherein the bottom side of the at least one printed circuit board substantially may be directed towards the bottom side of the at least one housing. Preferably, the magnetic sheet is embedded between the at least one electronic circuit and the at least one antenna element. Hereby, the at least one electronic circuit may be efficiently shielded from the at least one antenna element. Further, a misalignment of the different components arranged inside the at least one housing during the usage of the implantable hearing device may be avoided and the production process of the implantable hearing device may be simplified.

At least one magnet may be arranged substantially between the at least one implant antenna element and the top side of the at least one housing. The at least one magnet may be suited for attaching the at least one external device, in particular the at least one external hearing device, to the implantable hearing device. This allows for a reliable fixture of the at least one external device to the implantable hearing device. Preferably, the at least one magnet is arranged on top of the at least one printed circuit board.

The implantable hearing device may be a bone anchored hearing device, wherein the implantable hearing device further comprises an implant for implantation into a bone and an abutment for connection with the implant. In an exemplary embodiment, the abutment comprises a plastic and/or metal and/or is applied onto the implant. Thereby, in an exemplary embodiment, the abutment allows for transferring vibration from the implant hearing device, in particular via a coupling means, through the abutment and to the skull of the user. Using a metal is advantageous in terms of vibration properties and robustness of the abutment. Using plastic is advantageous in terms of light weight of the bone anchored hearing device. The bone anchored hearing device is adapted to be worn in any known way. This may include arranging a unit, in particular parts of or the electromagnetic vibrator, of the bone anchored hearing device attached to a fixture implanted into the skull bone, or arranging a unit, in particular parts of or the electromagnetic vibrator, of the bone anchored hearing device as an entirely or partly implanted unit.

The implantable hearing system may comprise at least one housing, at least one energy supply, at least one microphone and at least one external antenna element for inductively connecting the external hearing device to the implantable hearing device via a magnetic field. Hereby an at least partly implantable hearing system may be provided which reliably enhances the hearing capability of a user. The usage of the magnetic sheet may improve the duration of the energy supply, in particular of a battery, of the implantable hearing system.

The at least one implantable hearing device may comprise at least one magnet substantially between the at least one implant antenna element and the top side of the at least one housing, and the at least one external hearing device may comprise a corresponding magnet, wherein the at least one external hearing device and at least one the implantable hearing device are magnetically attachable to each other. Hereby, the at least one external device may be arranged in a convenient manner. Additionally, the at least one external device may easily be removed from the implantable hearing device.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
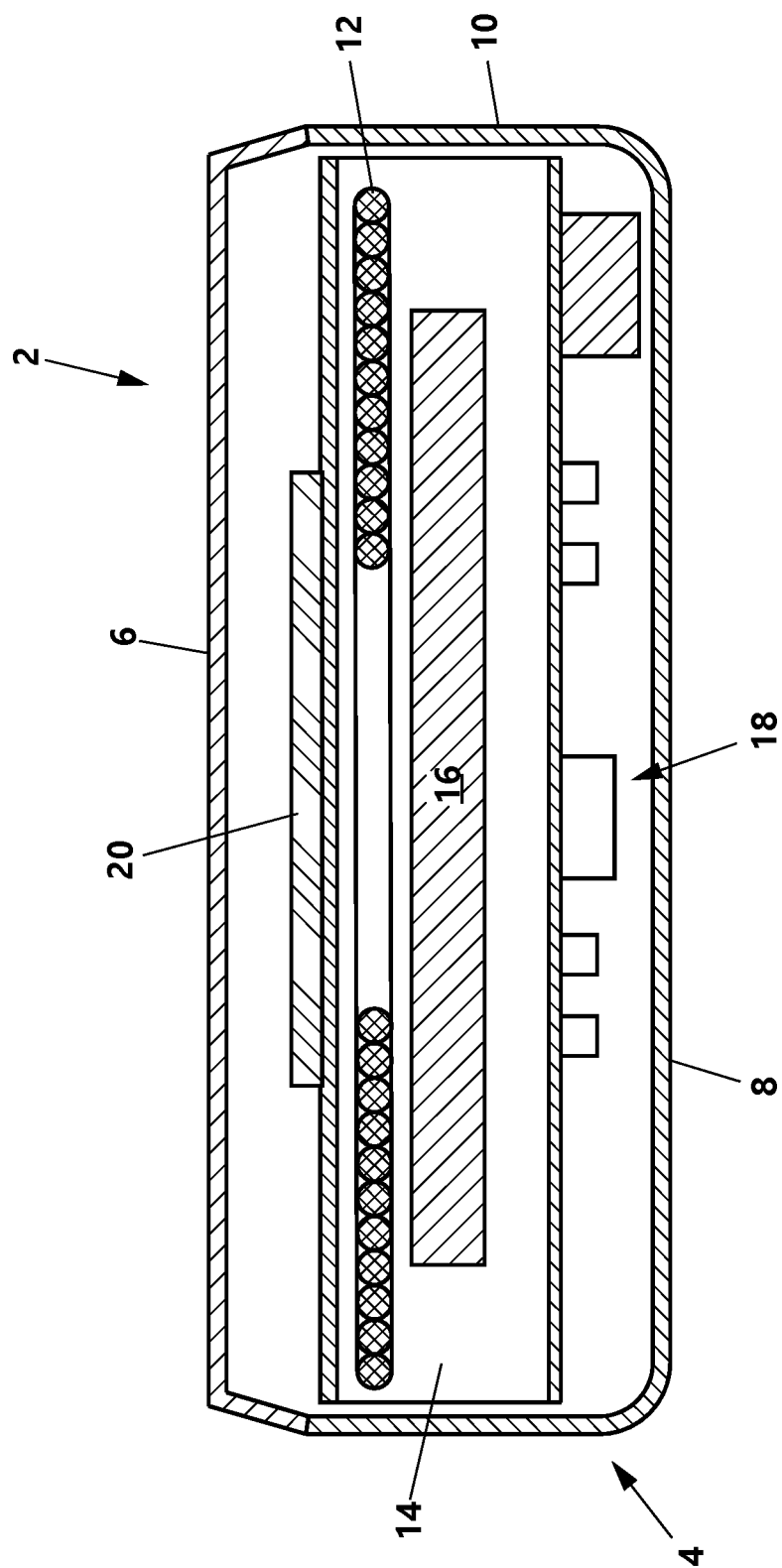
FIG. 1 schematically shows a cross sectional view of a first exemplary embodiment of an implantable hearing device.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The implantable hearing device and/or the implantable hearing system may be or include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. Such audible signals may be provided in the form of an acoustic signal transferred as mechanical vibrations to the user's inner ears through bone structure of the user's skull. 'Improving or augmenting the hearing capability of a user' may include compensating for an individual user's specific hearing loss.

The described implantable hearing device or the implantable hearing system may be part of a hearing system. Therein, a "hearing system" refers to a system comprising one or two hearing devices, and a "binaural hearing system" or a bimodal hearing system refers to a system comprising two hearing devices where the devices are adapted to cooperatively provide audible signals to both of the user's ears either by acoustic stimulation only, acoustic and mechanical stimulation, mechanical stimulation only, acoustic and electrical stimulation, mechanical and electrical stimulation or only electrical stimulation. The hearing system, the binaural hearing system or the bimodal hearing system may further include one or more auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of a remote control, a remote microphone, an audio gateway device, a wireless communication device, e.g. a mobile phone (such as a smartphone) or a tablet or another device, e.g. comprising a graphical interface, a public-address system, a car audio system or a music player, or a combination thereof. The audio gateway may be adapted to receive a multitude of audio signals such as from an entertainment device like a TV or a music player, a telephone apparatus like a mobile telephone or a computer, e.g. a PC. The auxiliary device may further be adapted to (e.g. allow a user to) select and/or combine an appropriate one of the received audio signals (or combination of signals) for transmission to the at least one hearing device. The remote control is adapted to control functionality and/or operation of the at least one hearing device. The function of the remote control may be implemented in a smartphone or other (e.g. portable) electronic device, the smartphone/electronic device possibly running an application (APP) that controls functionality of the at least one hearing device.

In general, an implantable hearing system includes i) an input unit such as a microphone for receiving an acoustic signal from a user's surroundings and providing a corresponding input audio signal, and/or ii) a receiving unit for electronically receiving an input audio signal. The implantable hearing system further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to (relatively) enhance a target acoustic source among a multitude of acoustic sources in the user's environment and/or to attenuate other sources (e.g. noise). In one aspect, the directional system is adapted to detect (such as adaptively detect) from which direction a particular part of the microphone signal originates. This may be achieved by using conventionally known methods. The signal processing unit may include an amplifier that is adapted to apply a frequency dependent gain to the input audio signal. The signal processing unit may further be adapted to provide other relevant functionality such as compression, noise reduction, etc. The output unit may include an output transducer for applying a mechanical stimulation transcutaneously or percutaneously to the skull bone or an electrical stimulation applied to auditory nerve fibers of a cochlea of the user. In some hearing implant systems, the output unit may include one or more output electrodes for providing the electrical stimulations such as in a Cochlear Implant, or the output unit may include one or more vibrators for providing the mechanical stimulation to the skull bone.

Now referring to FIG. 1, which illustrates a cross sectional view of a first exemplary embodiment of an implantable hearing device 2. The implantable hearing device 2 comprises a housing 4 which may include other components of the implantable hearing device. The housing 4 comprises a top side 6 which may be directed towards the skin of a user. The housing 4 further comprises a bottom side 8 which may be directed opposite to the top site 6. The top site 6 of the housing 4 substantially is of a ceramic material, wherein the bottom site 8 of the housing 4 substantially is of titanium or a titanium alloy. Additionally, the sides 10 of the housing 4 are similarly substantially made of titanium or a titanium alloy.

The implantable hearing device 2 further comprises an implant antenna element 12 which is embedded into a printed circuit board 14 and directed to the top side 6 of the housing 4. In the middle of the printed circuit board 14 a magnetic sheet in form of a ferrite sheet 16 is embedded. Additionally, the printed circuit board 14 comprises and electronic circuit 18 which is embedded and/or arranged on the side of the printed circuit board 14 which is directed towards the bottom side 8 of the housing 4. Further, a magnet 20 is arranged on the printed circuit board 14 between the printed circuit board 14 and the top side 6 of the housing 4.

The ferrite sheet 16 may be configured to affect the magnetic field of the antenna element 12 and redirect the magnetic field of the antenna element 12 into the direction of the top side 6 of the housing 4. Hereby, adverse influences of the part of the housing 4 which is substantially of titanium or a titanium alloy to the magnetic field of the antenna element 12 may be substantially avoided. By incorporating the antenna element 12, the ferrite sheet 16 and a part of the electronic circuit 18 into the printed circuit board 14, a small and compact implantable hearing device 2 may be provided.

Figure 2:
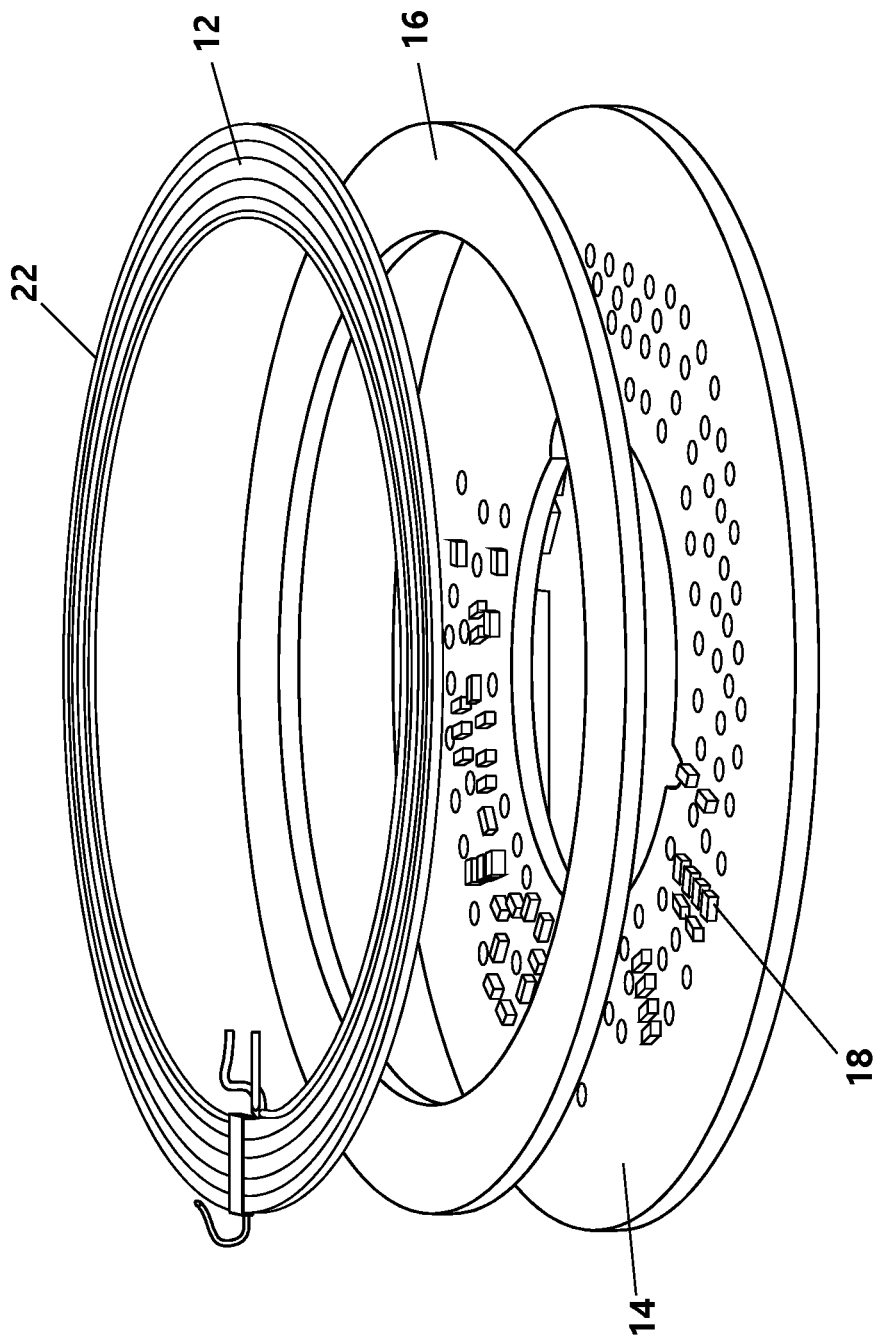
FIG. 2 schematically shows an exploded view of a part of a second exemplary embodiment of an implantable hearing device.

FIG. 2 illustrates an exploded view of a part of a second exemplary embodiment of an implantable hearing device 2. The printed circuit board 14, the ferrite sheet 16 and the antenna element 12 are formed substantially circular, in particular as a ring. The antenna element 12 forms a coil element 12 which comprises a plurality of windings of a litz wire 22. The outer diameter of the printed circuit board 14, the ferrite sheet 16 and the antenna element 12 may substantially corresponds to each other. Additionally, the inner diameter of the ferrite sheet 16 and the antenna element 12 may also substantially correspond to each other, wherein the printed circuit board 14 may comprise a smaller inner diameter. By positioning the ferrite sheet 16 between the antenna element 12 and the printed circuit board 14, the printed circuit board 14 may be shielded from the antenna element 12.

Figure 3:
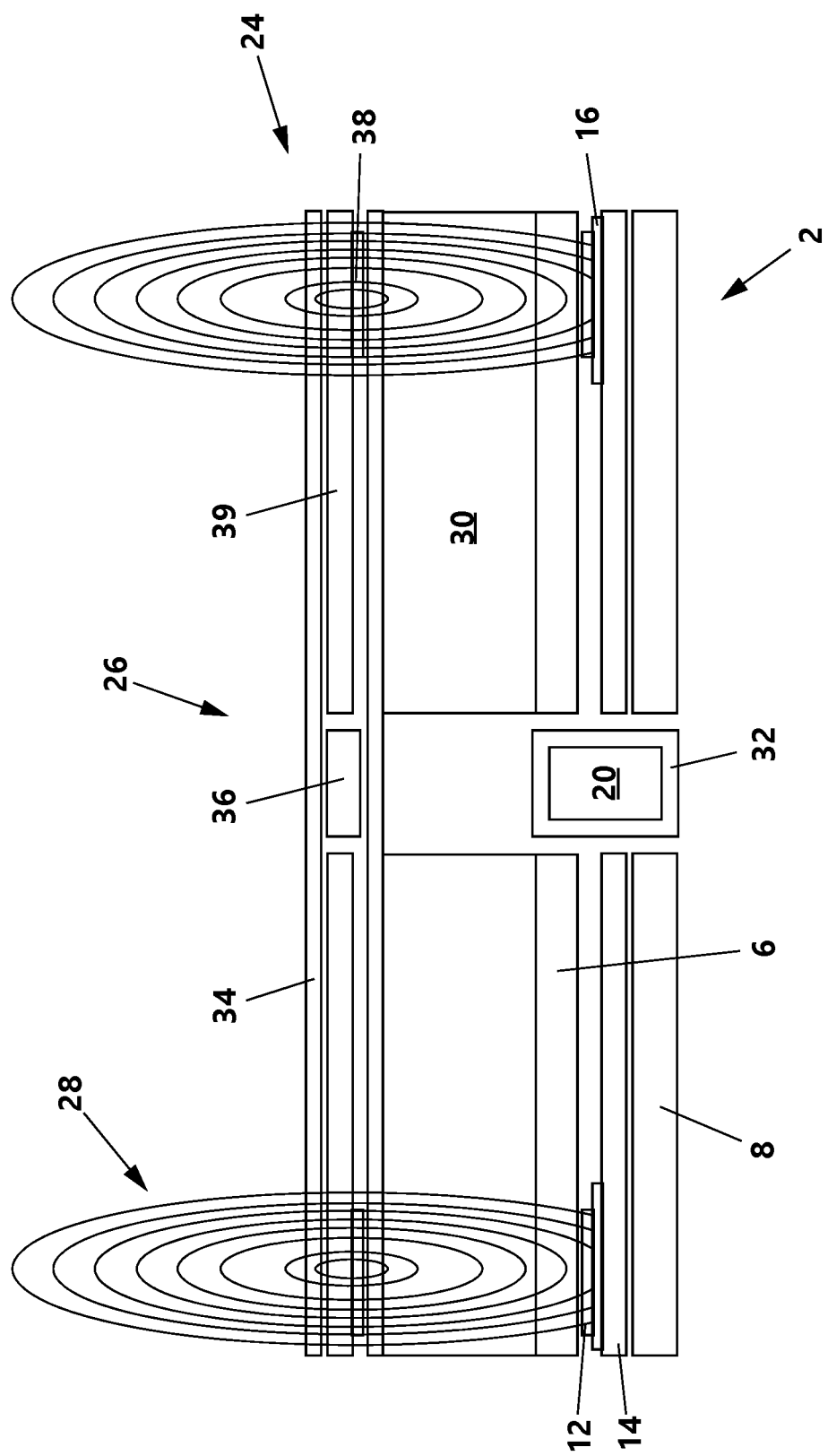
FIG. 3 schematically shows a view of a first exemplary embodiment of an implantable hearing system.

FIG. 3 schematically shows a view of a first exemplary embodiment of an implantable hearing system 24. The implantable hearing system 24 comprises an implantable hearing device 2 and one external hearing device 26. The implantable hearing device 2 may comprise a housing 4 with a bottom side 8 substantially of titanium or a titanium alloy. Above the bottom side 8 of the housing 4 a printed circuit board 14 may be arranged. On top of the printed circuit board 14 a ferrite sheet 16 and an antenna element 12 in form of an antenna coil are arranged. The top side 6 of the housing 4 directed to the skin 30 of a user may be substantially of ceramic material. In the center of the implantable hearing device a magnet 20 may be arranged, wherein the magnet 20 may comprise a magnet housing 32 which substantially is of titanium or a titanium alloy.

Above the skin 30 of a user the external hearing device 26 may be arranged. The external hearing device 26 may comprise a housing 34 which may for example substantially comprise a plastics material. Additionally, the external hearing device 26 may comprise an external magnet 36 for fixating the external hearing device 26 to the skin 30 of a user via the magnet 20. Further, an external antenna element 38 may be arranged on a printed circuit board 39 inside the housing 34 of the external hearing device 26.

Via the external antenna element 38 for example a magnetic field 28 may be induced in order connect the external antenna element 38 to the implant antenna element 12. As shown by the magnetic field lines, the ferrite sheet 16 may redirect the magnetic field lines in such a way that they are forwarded to the implant antenna element 12 and therefore may be correctly used. Hereby, the performance of the implantable hearing system 24 may be improved.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. An implantable hearing device for enhancing the hearing capability of a user comprising:
    at least one housing comprising a top side to be substantially directed towards the skin of a user and at least one bottom side to be substantially directed opposite to the top side,
    at least one implant antenna element for inductively connecting the implantable hearing device to an external device via a magnetic field,
    wherein the bottom side of the at least one housing at least partly is of metallic material, and
    wherein the top side of the at least one housing at least partly is of nonmetallic material, wherein,
    at least one magnetic sheet is arranged substantially between the at least one implant antenna element and the bottom side of the at least one housing,
    at least one printed circuit board arranged substantially between the at least one magnetic sheet and the bottom side of the at least one housing,
    wherein the at least one implant antenna, the at least one magnetic sheet, and the at least one printed circuit board are each formed as a ring,
    wherein the at least one magnetic sheet is configured to affect the magnetic field of the at least one implant antenna element.

2. Implantable hearing device according to claim 1, wherein,
    the bottom side of the at least one housing at least partly is of titanium, in particular that the bottom side of the at least one housing is substantially composed of titanium.

3. Implantable hearing device according to claim 2, wherein,
    the top side of the at least one housing at least partly is of ceramic material, in particular that the top side of the at least one housing is substantially composed of a ceramic material.

4. Implantable hearing device according to claim 2, wherein,
    the at least one magnetic sheet at least partly is of a ferrite material, in particular that the at least one magnetic sheet is substantially composed of a ferrite material.

5. Implantable hearing device according to claim 2, wherein,
    the at least one implant antenna element comprises at least one coil element, and
    the form of the at least one magnetic sheet substantially corresponds to the form of the at least one coil element.

6. Implantable hearing device according to claim 1, wherein,
    the top side of the at least one housing at least partly is of ceramic material, in particular that the top side of the at least one housing is substantially composed of a ceramic material.

7. Implantable hearing device according to claim 6, wherein,
    the at least one magnetic sheet at least partly is of a ferrite material, in particular that the at least one magnetic sheet is substantially composed of a ferrite material.

8. Implantable hearing device according to claim 6, wherein,
    the at least one implant antenna element comprises at least one coil element, and
    the form of the at least one magnetic sheet substantially corresponds to the form of the at least one coil element.

9. Implantable hearing device according to claim 1, wherein, the at least one magnetic sheet at least partly is of a ferrite material, in particular that the at least one magnetic sheet is substantially composed of a ferrite material.

10. Implantable hearing device according to claim 9, wherein, the at least one implant antenna element comprises at least one coil element, and the form of the at least one magnetic sheet substantially corresponds to the form of the at least one coil element.

11. Implantable hearing device according to claim 1, wherein, the at least one implant antenna element comprises at least one coil element, and the form of the at least one magnetic sheet substantially corresponds to the form of the at least one coil element.

12. Implantable hearing device according to claim 1, wherein, the at least one printed circuit board at least partly embeds the at least one implant antenna element and/or the at least one magnetic sheet.

13. Implantable hearing device according to claim 1, wherein, at least one magnet is arranged substantially between the at least one implant antenna element and the top side of the at least one housing, wherein the at least one magnet is suited for attaching the at least one external device, in particular the at least one external hearing device, to the implantable hearing device.

14. Implantable hearing device according to claim 1, wherein, the implantable hearing device is a bone anchored hearing device, wherein the implantable hearing device further comprises:

an implant for implantation into a bone, and an abutment for connection with the implant.

15. Implantable hearing system comprising:

at least one implantable hearing device according to claim 1, and at least one external hearing device for being inductively connected to the at least one implant antenna element.

16. Implantable hearing system according to claim 15, wherein, the at least one implantable hearing device comprises at least one magnet substantially between the at least one implant antenna element and the top side of the at least one housing, and the at least one external hearing device comprises a corresponding magnet, wherein the at least one external hearing device and at least one the implantable hearing device are magnetically attachable to each other.

17. Implantable hearing system according to claim 1, wherein, an outer diameter of the at least one printed circuit board, the at least one ferrite sheet, and the at least one antenna element substantially correspond.

18. Implantable hearing system according to claim 17, wherein, an inner diameter of the at least one ferrite sheet and the at least one antenna element substantially correspond.

* * * * *